United States Patent [19]

Beroza

[11] Patent Number: 4,715,848
[45] Date of Patent: Dec. 29, 1987

[54] GASTRO-INTESTINAL LAVAGE SYSTEM AND METHOD

[76] Inventor: Gregory A. Beroza, 16 Dikeman St., Hempstead, N.Y. 11550

[21] Appl. No.: 942,258

[22] Filed: Dec. 16, 1986

Related U.S. Application Data

[63] Continuation of Ser. No. 723,557, Apr. 15, 1985, abandoned.

[51] Int. Cl.[4] .............................................. A61M 1/00
[52] U.S. Cl. ...................................... 604/35; 604/43; 604/902
[58] Field of Search ...................... 604/35, 902, 43–45, 604/119, 268, 19, 22, 118, 266, 269

[56] References Cited

U.S. PATENT DOCUMENTS

| | | | |
|---|---|---|---|
| 386,603 | 7/1888 | Parsons . | |
| 701,075 | 5/1902 | McCully | 604/43 |
| 883,583 | 3/1908 | Stallsmith . | |
| 1,902,418 | 3/1933 | Pilgrim | 604/43 |
| 3,208,145 | 9/1965 | Turner . | |
| 3,429,313 | 2/1969 | Rananelli | 604/43 |
| 3,955,573 | 5/1976 | Hansen et al. | 604/92 |
| 4,002,170 | 1/1977 | Hansen et al. | 604/902 X |
| 4,061,146 | 12/1977 | Baeh et al. | 604/22 |
| 4,294,251 | 10/1981 | Greenwald et al. . | |
| 4,299,221 | 11/1981 | Phillips et al. . | |
| 4,468,216 | 8/1984 | Muto | 604/43 |

FOREIGN PATENT DOCUMENTS 753434 2/1978 U.S.S.R. .................. 604/27

Primary Examiner—Stephen C. Pellegrino
Attorney, Agent, or Firm—Thomas R. Morrison

[57] ABSTRACT

A gastro-intestinal lavage apparatus in which a hollow nozzle is inserted within a body cavity, said nozzle having an opening in the side thereof to permit debris in the body cavity to be pulled into a chamber within the nozzle. A source of reduced gas pressure is connected to the chamber at the exit end and a source of liquid under pressure is led into the chamber to direct a stream of liquid across the window and toward the reduced pressure source to break up the debris entering the chamber and increase the flow of said debris into and out of said chamber.

5 Claims, 4 Drawing Figures

GASTRO-INTESTINAL LAVAGE SYSTEM AND METHOD

This is a continuation of application Ser. No. 723,557 filed Apr. 15, 1985, now abandoned.

BACKGROUND OF THE INVENTION

This invention relates generally to a gastro intestinal lavage system useful in various applications wherein it is desired to fragment food and like debris present in a body cavity or in another enclosure by directing a fluid under pressure on the debris to fragment it and thereby remove the fragmented debris by an aspiration step. The invention is also concerned with a lavage method for removing debris from a body cavity or other enclosures.

The invention in particular relates to an equine gastro-intestinal lavage system and a method of lavage.

The invention also provides an improved nozzle for use in lavage apparatus.

The art to which this invention relates is illustrated by a number of patents describing various systems for removing debris and fluids from human and other body cavities. This background disclosure is restricted to those which are believed most relevant.

U.S. Pat. No. 386,603 which discloses a stomach pump having an air pump, a first flexible tube connected to the intake side of the air pump and a second flexible tube coupled to the exit port of the air pump. A first receptical is provided to receive the free end of the first tube and a second receptical receives the free end of the second flexible tube therein. An elongated compound rigid tube having two elongated chambers therein is insertable in the stomach. A flexible tube interconnects one of the rigid tube chambers with the first receptical and another flexible tube interconnects the other rigid tube chamber to the second receptical. The rigid tube walls are provided with apertures along each of the elongated chambers. When the pump is operated, a fluid in the second receptacle is sprayed or sprinkled into the stomach and the reduced pressure in the other elongated chamber draws the contents of the stomach into the second aperture from which it is led into the first receptacle.

U.S. Pat. No. 701,075 describes a catheter for the removal or provision of a fluid into the body comprising two half round tubes secured together along their flat sides and forming an inlet passage extending through the instrument and a return passage lying adjacent to and to one side of the inlet passage.

U.S. Pat. No. 883,583 describes a stomach pump comprising an eduction tube circular in cross-section and internally unobstructed from end to end, and an induction tube secured to the first tube with the passage through the tubes from end to end, including the terminals, the internal passages of each tube being of the same diameter throughout.

U.S. Pat. No. 3,208,145 relates to an aspirating hand piece with controls for vacuum air and water. The point of novelty of this apparatus is a hand piece formed to be gripped in the fingers of the hand of an operator to control the various functions of the device. The apparatus is for dental use.

U.S. Pat. No. 4,294,251 describes a suction lavage system incorporating a pulsating water lavage device in combination with a suction system to improve the interface between a prosthesis and the interdigitating network of cancellous bone in which it is secured with cement.

Finally, U.S. Pat. No. 4,299,221 illustrates an irrigation-suction tool incorporating an air pressure conduit connectible to an air pressure source, a separate suction conduit connectible to a suction source, and an irrigant liquid conduit connectible to an irrigant liquid source in which there is provided a tip unit having a forward end placeable adjacent the operating site and comprising hollow elongate suction and irrigant liquid tips for respectively removing liquid material from the operating site and supplying irrigant liquid thereto.

SUMMARY OF THE INVENTION

The invention relates to a lavage apparatus comprising a hollow nozzle having a fluid bearing and an aspirating tube communicating with a chamber of the nozzle. The tubes are connectible the one to a source of sub-atmospheric pressure and the other to a fluid source such as water at city pressure, the water tube being of considerably smaller cross-section than the aspirating tube. The water jets across an intake window in the wall of the nozzle within the chamber and breaks up food and like debris while the Venturi effect of the water breaks up and moves the food debris into the aspirating tube. The aspirating tube is connected via a valve assembly to a collecting drum which is also maintained under reduced pressure with a suction pump. The nozzle has a rounded, smooth front end to facilitate insertion in the mouth or other cavity of an animal.

BRIEF DESCRIPTION OF THE DRAWINGS

The present invention is further illustrated in nonlimiting fashion by the accompanying drawings in which like reference characters refer to the same or like parts and wherein.

DETAILED DESCRIPTION OF THE INVENTION

Figure 1:
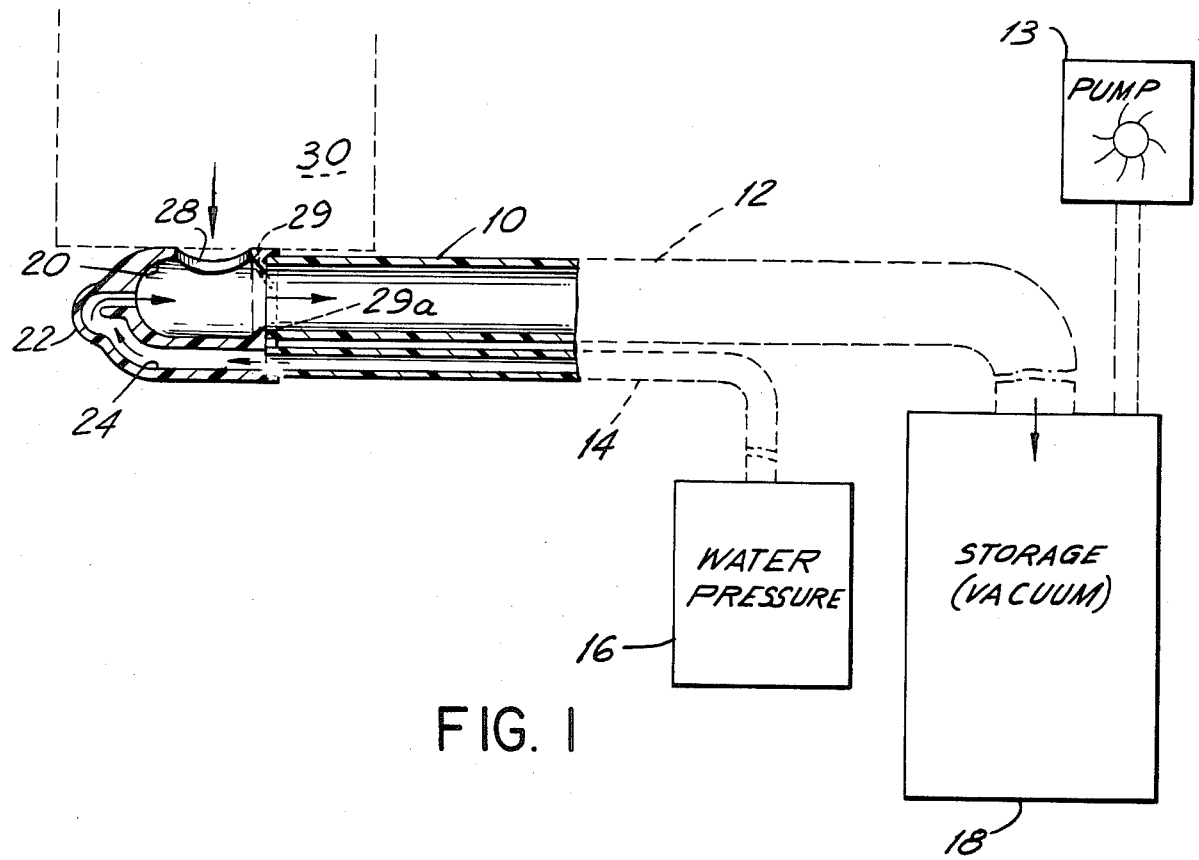
FIG. 1 is a somewhat diagrammatic, partly cross-sectional view of the gastro-intestinal lavage apparatus of the invention.

The invention will be described mainly with respect to an embodiment thereof particularly adapted to equine gastric and intestinal lavage to remove gastric debris from a filled stomach by passage down an anesthetized horse's esophagus via the mouth. This procedure is necessary at the time of abdominal surgery on the animal. The exemplary apparatus is also suitable for cleaning the large bowel including the cecum when it is entered into the pelvic flexure of the large or the apex of the cecum by an enterotomy. The apparatus also is used to cleanse the large bowel of its gastric debris which are, due to impaction, loss of ability for evacuation or other conditions necessitating decompression of the large bowel. The use of this invention is most pertinent to horses which, unlike other animals, are unable to regurgitate to clear foreign matter which may have become lodged in their stomachs. The apparatus shown is also easily and safely entered through the exteriorized large bowel and into the abdominal cavity.

Referring specifically to the drawings, the apparatus 10 includes a nozzle 11, connected to a suction tube 12 and a fluid or water bearing tube 14. In this embodiment these are provided as separate tubes but it is understood that a one-piece tube having side-by-side passageways can also be used. The inside diameter of the suction tube is from 3 to 5 times larger than that of the water tube 14. One end of the suction tube 12 is connected to a storage tank 18 which is maintained under reduced pressure by a vacuum pump 13. The overall suction employed ranges from about 5 to about 20 inches. The water tube 14 is connected to a source of water under pressure 16 such as city water under approximately 55 to 65 psi. Both tubes lead into a nozzle aspirating chamber 20 which terminates at its front end in a rounded nozzle portion 22 and communicates with the interior of the body cavity by means of a window 28 in the nozzle wall. Water tube 14 communicates with an elongated passageway 24 in the nozzle 11 which is doubled back upon itself near the proximal end of the nozzle to lie substantially in line with the longitudinal axis of a port 29 short of the rounded end of the nozzle and provides an opening 26 for directing water in the form of a pressurized stream across the inside of the aspirating chamber 20 into the entrance portion 47 of the substantially circular port 29 in the nozzle 11. The port 29 has an exit portion 29a which abuts the inner extremity of tube 12. Sharp edges are eliminated as much as possible from the outer surface of suction nozzle 11 and the aspirating chamber 20. Preferably, the chambered nozzle and tubes are made of smooth plastic such as polyethylene or "Teflon" or the like. In one embodiment, the nozzle 11 and chamber portion will not exceed two inches in length with the aspirating chamber 20 not to be less than ¾ of an inch wide, 1 inch long with a ⅜ inch port 29. The nozzle wall section is preferably not less than ¼ of an inch throughout. The suction tubing 12 preferably has an internal diameter of ⅝ of an inch, an outside diameter of 13/16 of an inch and a wall thickness of 3/32 of an inch. The water tubing 14 preferably has an internal diameter of ¼ of an inch, an outside diameter of 5/16 of an inch and its wall thickness is 1/16 of an inch wide. It is important that the walls of the nozzle 11 and of the chamber 20 be very thin yet strong enough to withstand the suction, the water pressure and handling wear.

From the above description it will be seen that the operation of the apparatus is to draw up gastric contents into the chamber 20 through the window 28 and to break up the debris by impacting it with a stream of a high volume of water under considerable pressure and substantial velocity. The Venturi effect of the stream of water directed across the chamber 20 at the port 29 serves to further draw the material within the body cavity into the aspirating chamber 20. It is necessary that a hard stream and not merely a spray of water contact the debris 30 in the chamber, as shown in FIG. 2.

Figure 2:
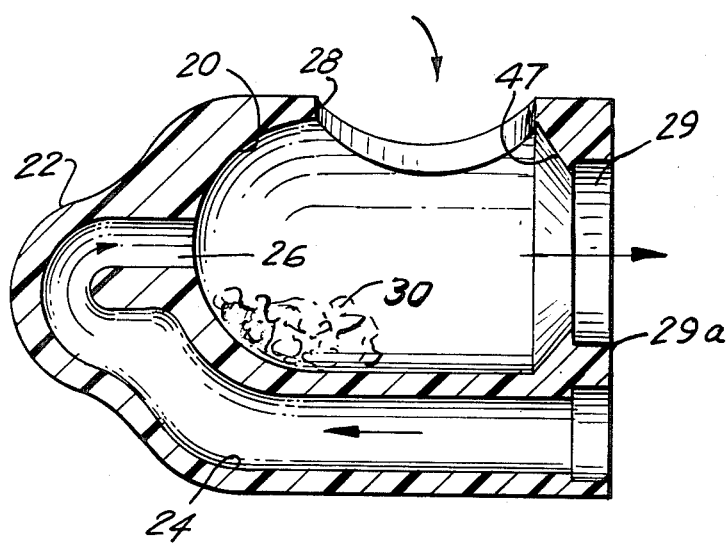
FIG. 2 is a cross-sectional view of the nozzle of the invention.
Figure 3:
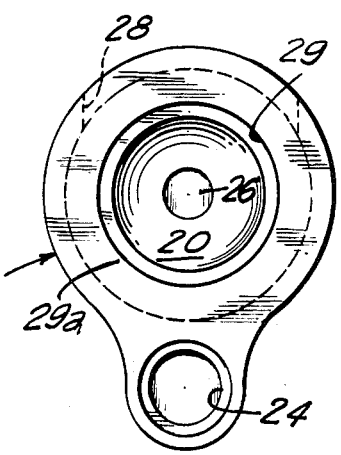
FIG. 3 is an end view taken from the right side of FIG. 2.

As illustrated in greater detail in FIG. 2, the volume inside chamber 20 is greater than the inside diameter of port 29 of suction tube 12. This makes it possible to take advantage of the Venturi effect by the cooperation of the water stream and the suction tube 12 to move a slurry of waste from a larger enclosure into a tube of slightly smaller diameter. As this occurs the velocity of the slurry and the force under which it travels further break up the slurry into finer pieces of waste debris which are carried away in the suction tubing 12 to the storage container 18 which is also under reduced pressure.

The above described apparatus in the dimensions indicated is particularly designed for insertion through a horses mouth.

Figure 4:
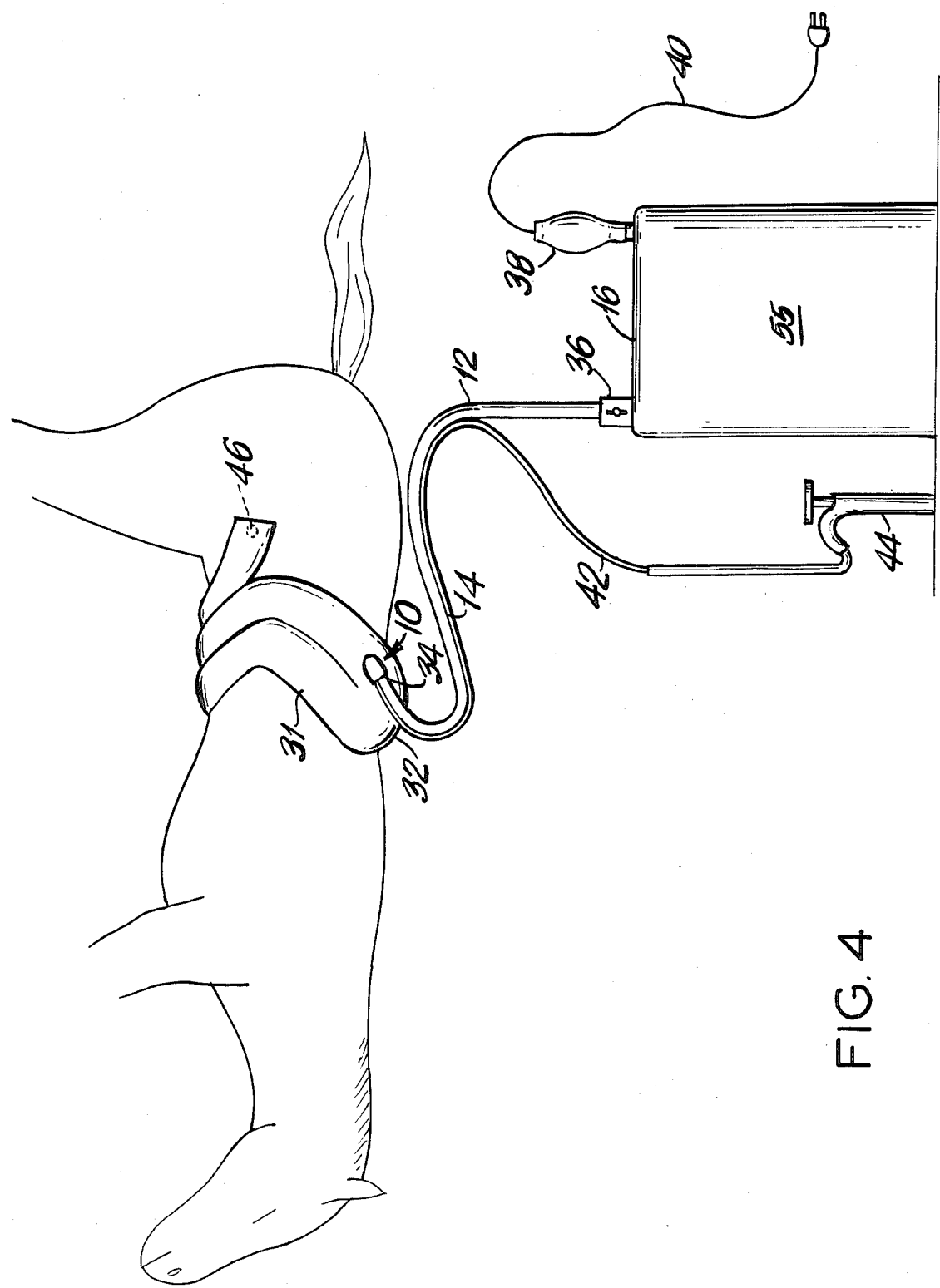
FIG. 4 is a diagrammatical view showing use of the invention for gastro-intestinal lavage.

Referring now to FIG. 4 there is shown a modification of the present apparatus suitable for gastro-intestinal lavage which is adapted to be entered into the pelvic flexure of the large bowel or the apex of the cecum via an enterotomy and which is held in place by a the purse string suture 31 (well-known in the veterinary surgery art).

As shown, the apparatus 10 which here includes two tubes 12 and 14 has been inserted by an incision 32 and is held in place by the purse string suture 34. Tube 12 is connected to storage container 16 through an on-and-off valve 36. The container 16 communicates with a suction pump 38 which in this case is an electrical pump connected by connection 40 to an electrical outlet.

Water supply tube 44 is connected to a garden hose 42 which is itself connected to a source of water at city pressure 44. FIG. 4 shows also at 46 an alternate site for making an incision to pass the apparatus through the skin, this site being the exteriorized apex of the horse's cecum.

While the present invention has been described with respect to its uses for equine gastro and gastro-intestinal lavage, those skilled in the art will readily appreciate that the general principle thereof is generally applicable to general waste disposal, to human medicine, as well as to waste disposal and handling of other fluids in outerspace vehicles. Accordingly, where the apparatus is to be used in non-living organisms, it will be apparent to those skilled in the art that instead of water pressure, air pressure may be used to break up debris. Similarly, other fluids can be used instead of water in the invention where appropriate.

Having thus disclosed the invention, what is claimed and desired to be protected by Letters Patent is:

1. A gastric lavage device comprising:
    a nozzle;
    an aspirating chamber in said nozzle;
    a window in a side of said aspirating chamber, effective for communicating with a body cavity;
    an exit port in a rear portion of said nozzle;
    an opening in a forward end of said aspirating chamber, said opening being directed toward said exit port from front to rear across said aspirating chamber;
    means for connecting a source of pressurized liquid to said opening;
    said opening and said source of pressurized liquid being effective in combination to direct a hard stream of said liquid through said aspirating chamber toward said exit port, whereby debris in said aspirating chamber is broken up and urged toward said exit port;
    means for creating a reduced pressure at said exit port, whereby debris in said body cavity may be drawn through said window into said aspiration chamber, therein to be broken up by said hard stream of liquid and removed through said exit port.

2. A gastric lavage device according to claim 1, wherein:
    said aspirating chamber includes a first inner diameter transverse to a direction of said hard stream of said liquid;

said exit port includes second inner diameter; and
said second inner diameter being substantially smaller than said first inner diameter, whereby a Venturi effect aids in urging said debris through said exit port.

3. A gastric lavage device according to claim 2, wherein said exit port includes:
an entrance portion and an exit portion;
said entrance portion being proximal said aspirating chamber;
said exit portion being distal said aspirating chamber; and
said entrance portion being a truncated cone reducing in diameter from said aspirating chamber to said exit portion, whereby said Venturi effect is enhanced.

4. A gastric lavage device according to claim 1, wherein said nozzle further includes:
a smoothly rounded forward end portion;
an elongated passageway parallel to said aspirating chamber;
a rear end of said elongated passageway including means for connecting said source of pressurized liquid to said nozzle; and
a forward end of said passageway being curved backward to meet said opening, whereby said source of pressurized liquid is connected to said opening for the formation of said hard stream of liquid.

5. A method for removing debris from a body cavity comprising:
placing a nozzle having an aspirating chamber therein in said body cavity;
comunicating said aspirating chamber with said body cavity through a window in a side thereof;
directing a hard flow of a pressurized liquid across said aspirating chamber from an opening in a front of said nozzle to an exit port in a rear portion of said nozzle;
said hard flow having a flow and a volume effective for urging debris in said aspirating into said exit port; and
creating a reduced pressure at said exit port, whereby debris in said body cavity may be drawn through said window into said aspiration chamber, and therein to be broken up by said hard stream of liquid and removed through said exit port.

* * * * *